US008116985B1

(12) United States Patent
Johnson et al.

(10) Patent No.: US 8,116,985 B1
(45) Date of Patent: Feb. 14, 2012

(54) REAL TIME SAMPLING, MONITORING AND EXPOSURE CONTROL OF TEST ANIMALS

(75) Inventors: Jerry D. Johnson, Dublin, OH (US);
Steven W. Graves, Powell, OH (US);
Seongwon Hong, Dublin, OH (US);
Herbert S. Bresler, Bexley, OH (US);
Michael J. Brooker, Westerville, OH (US); R. Mark Gritz, Fairfax, VA (US)

(73) Assignee: Battelle Memorial Institute, Columbus, OH (US)

( * ) Notice: Subject to any disclaimer, the term of this patent is extended or adjusted under 35 U.S.C. 154(b) by 408 days.

(21) Appl. No.: 11/687,938

(22) Filed: Mar. 19, 2007

Related U.S. Application Data

(60) Provisional application No. 60/783,652, filed on Mar. 17, 2006, provisional application No. 60/783,653, filed on Mar. 17, 2006.

(51) Int. Cl.
*G01N 33/48* (2006.01)
(52) U.S. Cl. .......................................................... 702/19
(58) Field of Classification Search ...................... 702/19
See application file for complete search history.

(56) References Cited

U.S. PATENT DOCUMENTS

| | | | |
|---|---|---|---|
| 3,674,011 A | 7/1972 | Michel et al. | |
| 3,908,657 A | 9/1975 | Kowarski | |
| 4,008,717 A | 2/1977 | Kowarski | |
| 4,077,395 A | 3/1978 | Woolner | |
| 4,087,864 A | 5/1978 | LaBove et al. | |
| 4,127,111 A | 11/1978 | Drolet | |
| 4,348,985 A | 9/1982 | Leong | |
| 4,520,808 A | 6/1985 | LaBauve | |
| 4,582,055 A | 4/1986 | McDougal et al. | |
| 4,657,027 A | 4/1987 | Paulsen | |
| 4,669,458 A | 6/1987 | Abraham et al. | |
| 4,696,309 A | 9/1987 | Stephan | |
| 4,721,060 A | 1/1988 | Cannon et al. | |
| 4,784,157 A | 11/1988 | Halls et al. | |
| 4,833,384 A | 5/1989 | Munro et al. | |
| 4,917,046 A | 4/1990 | Spengler | |
| 5,002,066 A | 3/1991 | Simpson et al. | |
| 5,035,865 A | 7/1991 | Inaba et al. | |
| 5,037,396 A | 8/1991 | Streeter | |
| 5,066,283 A | 11/1991 | Skrabal | |
| 5,109,797 A | 5/1992 | Briant et al. | |
| 5,153,828 A | 10/1992 | Inoue et al. | |
| 5,297,502 A | 3/1994 | Jaeger | |
| 5,325,867 A | 7/1994 | Skrabal et al. | |
| 5,507,299 A | 4/1996 | Roland | |
| 5,626,130 A | 5/1997 | Vincent et al. | |
| 5,871,699 A | 2/1999 | Ruggeri | |
| 5,885,261 A | 3/1999 | Longo et al. | |
| 6,004,292 A | 12/1999 | Battiato et al. | |
| 6,113,554 A | 9/2000 | Gilcher et al. | |
| 6,358,218 B1 | 3/2002 | Want et al. | |
| 6,402,702 B1 | 6/2002 | Gilcher et al. | |
| 6,520,930 B2 | 2/2003 | Critchlow et al. | |
| 6,616,616 B2 | 9/2003 | Fritz et al. | |
| 6,681,404 B1 | 1/2004 | Adlard et al. | |
| 6,736,783 B2 | 5/2004 | Blake et al. | |
| 7,063,684 B2 | 6/2006 | Moberg | |
| 7,384,409 B2 | 6/2008 | Fischer et al. | |
| 7,445,604 B2 | 11/2008 | Cash | |
| 7,621,896 B2 | 11/2009 | Rose | |
| 7,665,424 B2 | 2/2010 | Denault et al. | |
| 2002/0055690 A1 | 5/2002 | Want et al. | |
| 2002/0169394 A1 | 11/2002 | Eppstein et al. | |
| 2003/0199897 A1 | 10/2003 | Boecker et al. | |
| 2004/0052730 A1* | 3/2004 | Hochman | 424/9.2 |
| 2004/0249308 A1 | 12/2004 | Forssell | |
| 2005/0015019 A1 | 1/2005 | Honda et al. | |
| 2005/0228313 A1 | 10/2005 | Kaler et al. | |
| 2006/0102091 A1 | 5/2006 | Kissinger | |
| 2006/0173378 A1 | 8/2006 | Fonss | |
| 2006/0229531 A1 | 10/2006 | Goldberger et al. | |
| 2006/0282060 A1 | 12/2006 | Fujii | |
| 2007/0123801 A1 | 5/2007 | Goldberger et al. | |
| 2007/0179435 A1 | 8/2007 | Braig et al. | |
| 2007/0179436 A1 | 8/2007 | Braig et al. | |
| 2007/0191716 A1* | 8/2007 | Goldberger et al. | 600/481 |
| 2007/0191735 A1 | 8/2007 | Hansson | |
| 2008/0010717 A1 | 1/2008 | King | |
| 2008/0058727 A1 | 3/2008 | Domash et al. | |
| 2008/0064985 A1 | 3/2008 | Madonia | |
| 2008/0071224 A1 | 3/2008 | Forsyth | |
| 2008/0200837 A1 | 8/2008 | Frazier et al. | |
| 2008/0200838 A1 | 8/2008 | Goldberger et al. | |
| 2009/0054844 A1 | 2/2009 | Alyea et al. | |
| 2009/0156922 A1 | 6/2009 | Goldberger et al. | |
| 2010/0145281 A1 | 6/2010 | Denault et al. | |
| 2010/0191190 A1 | 7/2010 | Nokes, Jr. et al. | |

FOREIGN PATENT DOCUMENTS

| | | |
|---|---|---|
| FR | 2621696 | 4/1989 |
| FR | 2599618 | 12/1989 |
| JP | 029367 | 2/2007 |
| WO | 2005082251 | 9/2005 |
| WO | 2006132571 | 12/2006 |
| WO | 2007064596 | 6/2007 |

* cited by examiner

OTHER PUBLICATIONS

Bentson et al., "A Remote-Controlled Device for Long-Term Blood Collection from Freely Moving, Socially Housed Animals," Behav. Res. Methods Instrum. Comput., Aug. 1999, 31(3), pp. 455-463.

*Primary Examiner* — Jerry Lin

(74) *Attorney, Agent, or Firm* — MacMillan, Sobanski & Todd, LLC

(57) ABSTRACT

An automated blood or bodily fluid sampling machine for collecting, measuring and monitoring real time samples from test animals during dosing of the animals, automatically provides real-time adjustment of dosing during testing. Such automated blood or bodily fluid sampling is performed in tandem with implanted physiological monitoring devices to monitor biological and physiological parameters in restrained or freely-moving test animals. The real-time feedback provides for dosing adjustment within testing protocols.

18 Claims, 7 Drawing Sheets

○ OBSERVED
— PREDICTED

REAL TIME SAMPLING, MONITORING AND EXPOSURE CONTROL OF TEST ANIMALS

PRIORITY CLAIM TO PREVIOUSLY FILED APPLICATIONS

The present invention claims the benefit of U.S. Provisional Patent Application Ser. No. 60/783,652, filed Mar. 17, 2006, entitled "Automatic Blood Sampling and Exposure Control of Test Animals", and U.S. Provisional Patent Application Ser. No. 60/783,653, filed Mar. 17, 2006, entitled "Real Time Cardiotelemetry and Toxicokinetics from a Freely Moving Rat".

The present invention relates to use of an automated blood or bodily fluid sampling machine for collecting, measuring and monitoring real time samples from test animals during dosing of the animals, and automatically providing real-time adjustment of dosing during testing. Such automated blood or bodily fluid sampling is performed in tandem with implanted physiological monitoring devices to monitor biological and physiological parameters in restrained or freely-moving test animals.

BACKGROUND OF THE INVENTION

The use of animals for testing the safety, toxicity and efficacy of a wide variety of substances is well known. Routine testing is performed on animals that are restrained, as well as animals that are freely moving, and dosing may be achieved by inhalation, whole body exposure, injection, intravenous injection, ingestion, installation, implantation and other methods known in the art. Such testing has involved many species of animals up to non-human primates.

Prior to the advent of automated dosing and sample collection machines, multiple animals were needed in order to collect samples of blood or other bodily fluids, or to measure the physiological endpoints. However, both types of data have not been collected easily at the same time with the same animal. It remains a problem that in present animal testing protocols, measurements of certain physiological endpoints require periodic handling of test animals at time intervals, causing the animals to become stressed. As well, due to the demands of sample acquisition that results in sacrifice of animals, groups of animals need to be used. As a result, over the course of a study samples of fluids are required from different animals in the group that are sacrificed as a study progresses. As a result, it has been necessary to average test results from samples over the members of the group of test animals to obtain overall values, rather than have samples of blood and bodily fluids, as well as physiological data, from the same animal throughout a study.

These and other problems associated with test animal sampling and monitoring are overcome by the present invention.

SUMMARY OF THE INVENTION

In accordance with the present invention, multiple, serial samples of bodily fluids can be collected while the exposure to a test animal is in progress, thereby making it possible to measure the analyte(s) of interest so as to evaluate the exposure and/or effect(s) of the exposure.

The present invention overcomes these problems with test animal monitoring by using an automated dosing and blood or bodily fluid sampling machine for collecting multiple, serial samples of bodily fluids, or exhaled breath while the exposure to a test animal is in progress, thereby making it possible to measure the analyte(s) of interest and evaluate the exposure and/or effect(s) of the exposure in real time. The present invention further uses such automated dosing and a blood or bodily fluid sampling machine, or collection of exhaled breath in tandem with implanted physiological monitoring devices that are used to monitor various physiological endpoints for the purpose of evaluating whether a relationship exists between the dose, kinetics, and/or endpoints in a restrained or freely-moving, non-restricted test animal.

DETAILED DESCRIPTION OF THE PREFERRED EMBODIMENTS

Figure 1:
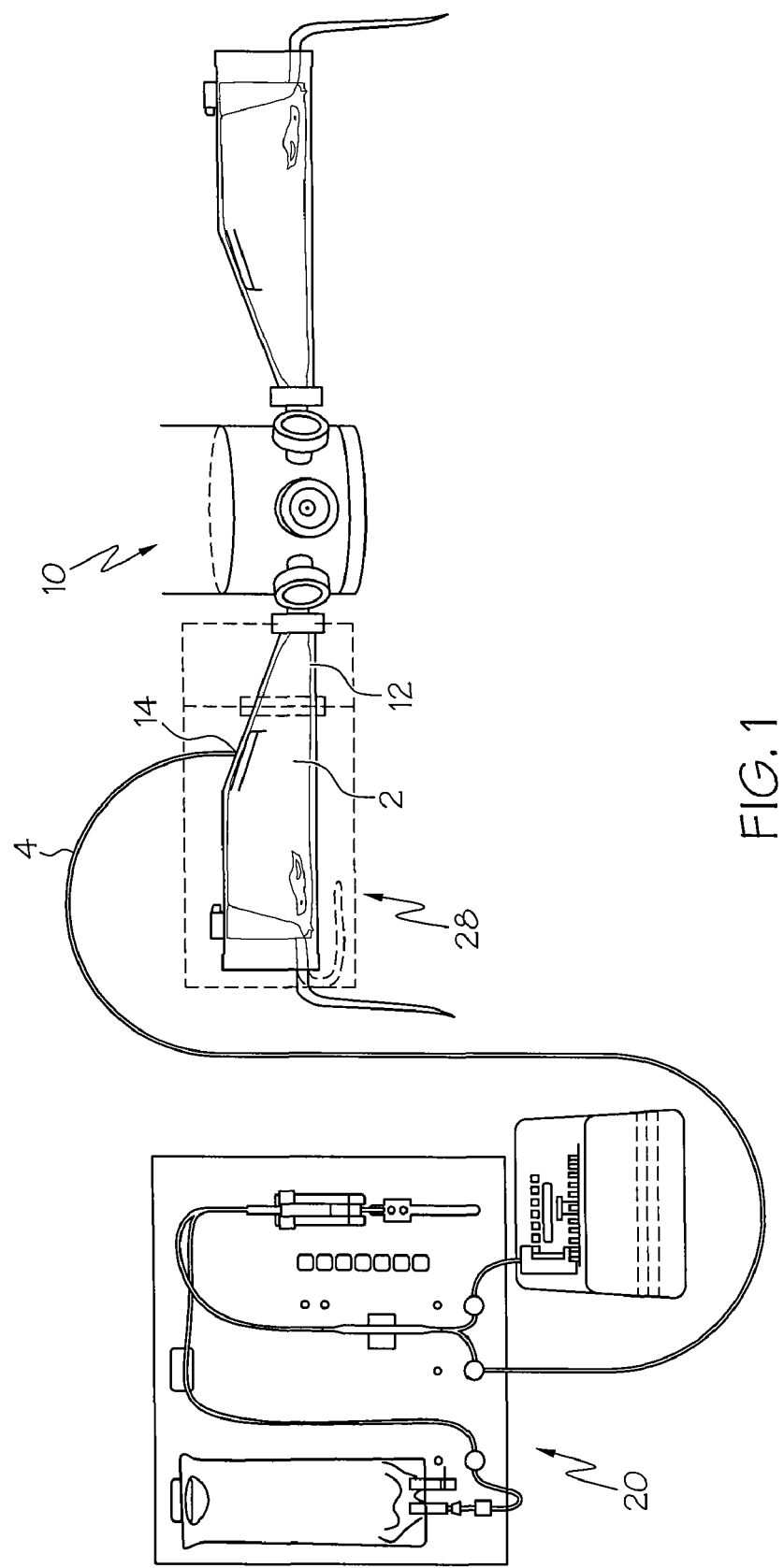
FIG. 1 shows the use of a catheter in an exposure system in accordance with the present invention.

In accordance with a first aspect of the present invention shown in FIG. 1, a test animal 2 restrained in an exposure system 10 is prepared for testing by surgically implanting an indwelling catheter 4 in the animal and exteriorizing it to an automated sample collection machine 20. The indwelling catheter 4 is surgically implanted in a specific blood vessel or tissue/organ of interest in the animal 2. The catheter 4 is designed to meet the needs of sample collection taking into account the animal, fluid, tissue or organ, and apparatus on which testing is occurring. The catheter 4 is passed through an opening, slot, longitudinal slit or aperture 14 in the exposure chamber 12, such as a nose-only restraint tube, which contains the test animal 2.

The nose-only restraint tube shown is merely representative of exposure chambers used for restraining test animals, and is not intended to limit the scope of the invention such an exposure chamber or to inhalation testing alone, and freely moving caged animals may also be fitted with such catheters 4. The aperture 14 is preferably sealed to preserve the integrity of the exposure chamber 12 using any of a variety of materials. By way of example and not intending to limit the scope of the present invention, the catheter 4 in aperture 14 may extended through a seal comprising opposing flexible surfaces, or opposing fibrous surfaces, or sealed with tape, sealing compounds, putty, grommets, o-rings or the like.

The catheter 4 extends to an automated sample collection machine 20, such as a blood or bodily fluid sampling device, by way of example and not limitation such as the Culex automatic sampling machine available from Bioanalytical Systems, Inc (BASi) W. Lafayette, Ind., which collects whole blood samples, or the BASi microdiffusion or microdialysis sampling machine for collection of bodily fluid samples from tissues or organs.

Because test animals 2 can typically include mice, rats, guinea pigs, rabbits, ferrets, dogs, pigs and other mammals up to non-human primates, as well as chickens and other birds, some commercially available catheters may be suitable for testing. However, specifically-designed catheters made by Culex or BASi may be needed to connect the Culex blood sampling or BASi microdiffusion or microdialysis machines to a particular animal. Typical for inhalation toxicology testing are rodents, restrained in nose-only restraint tubes, as representatively shown in FIG. 1.

Figure 3:
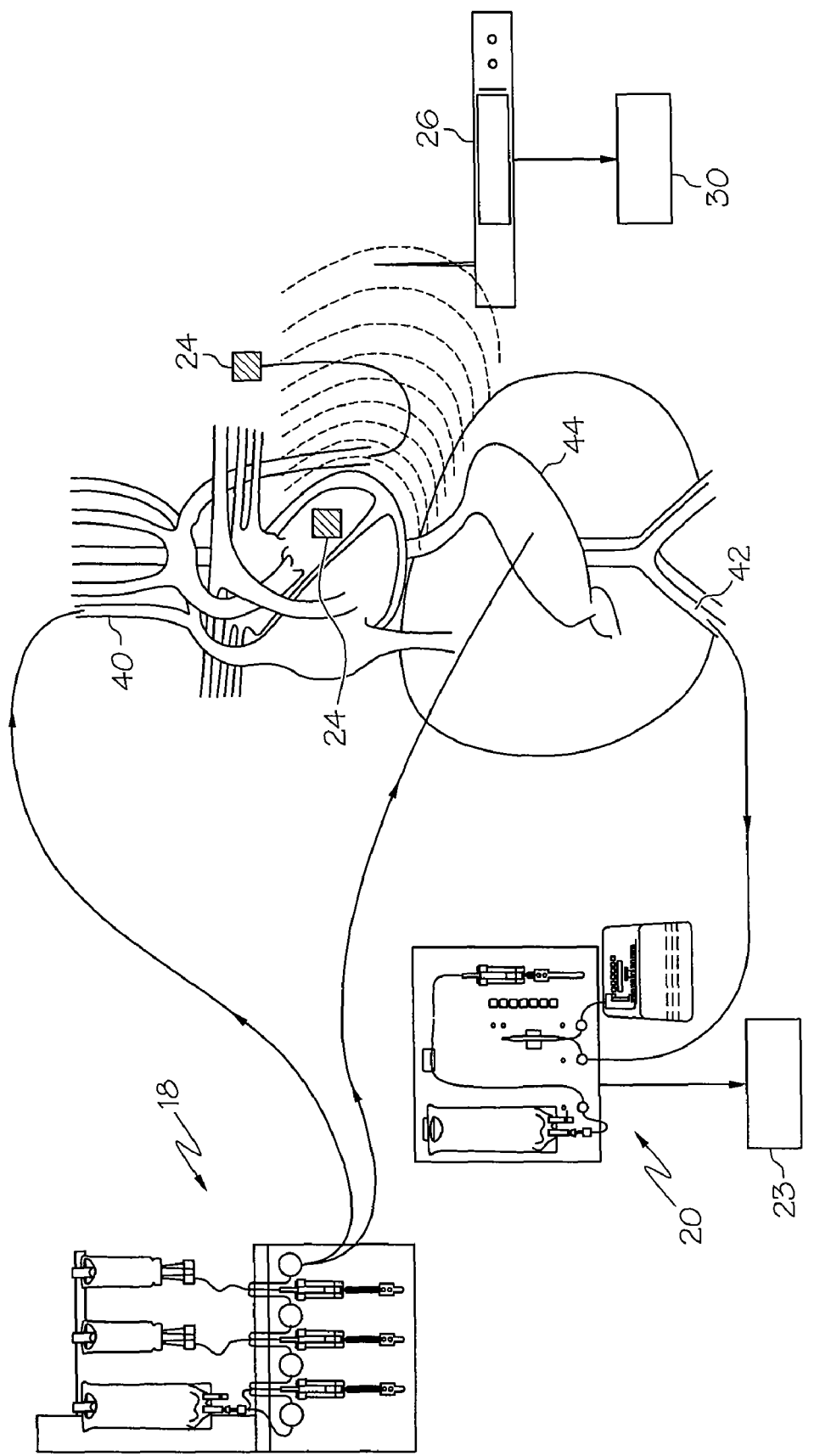
FIG. 3 shows a representative system for dosing, sampling and measurement in accordance with the present invention.
Figure 4A:
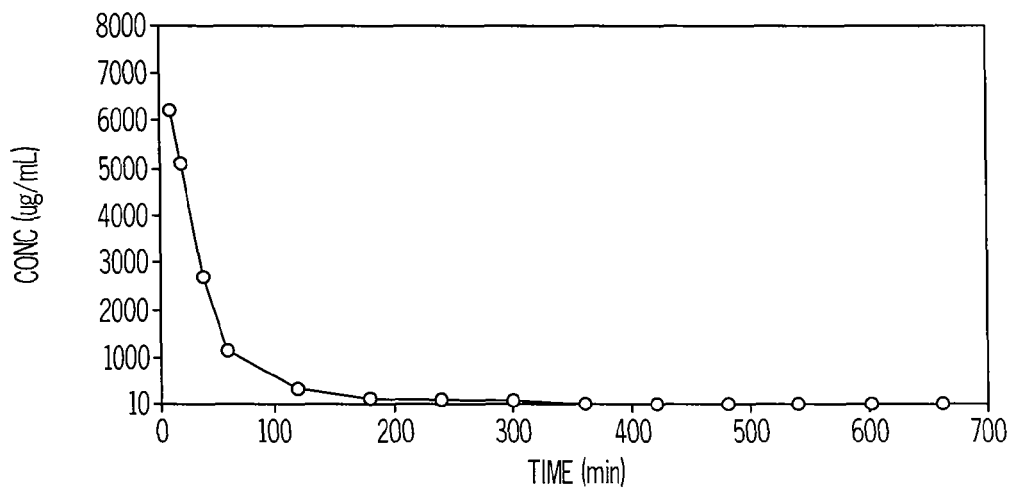
FIGS. 4A-4E show representative output from measurements made by physiological monitoring devices used to monitor a test animal.
Figure 4B:
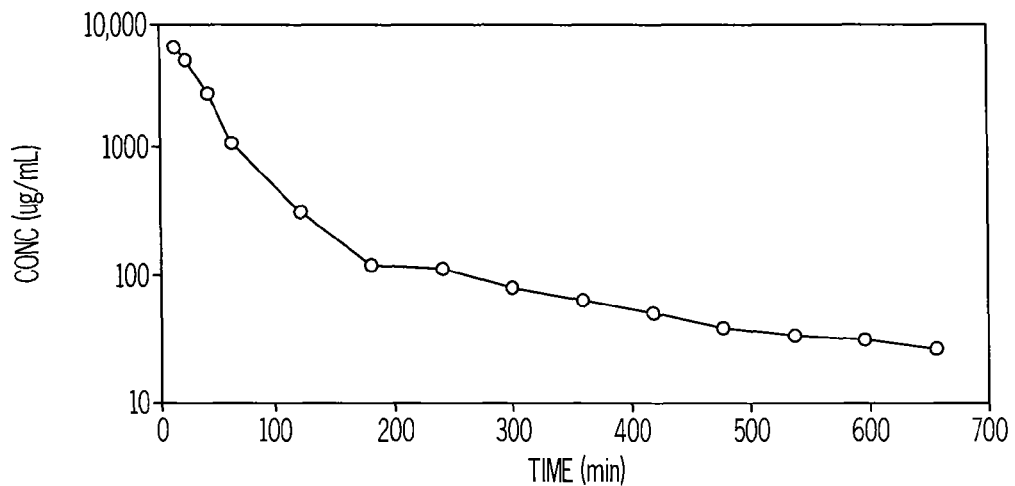
Figure 4C:
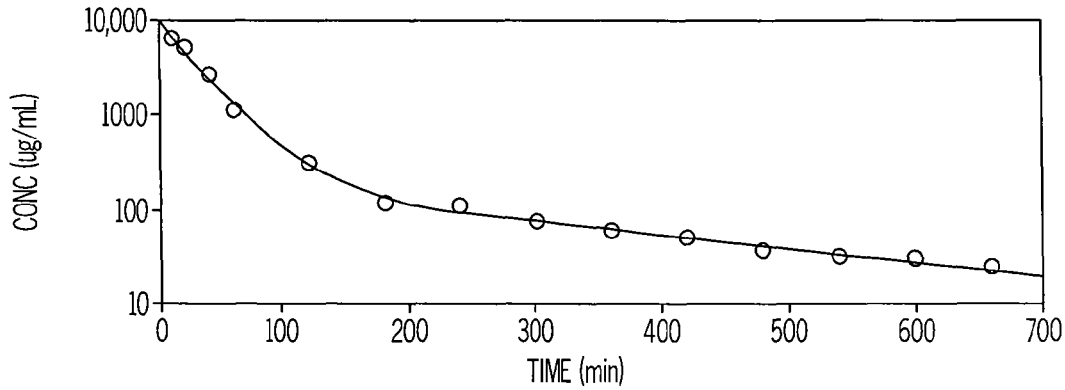
Figure 4D:
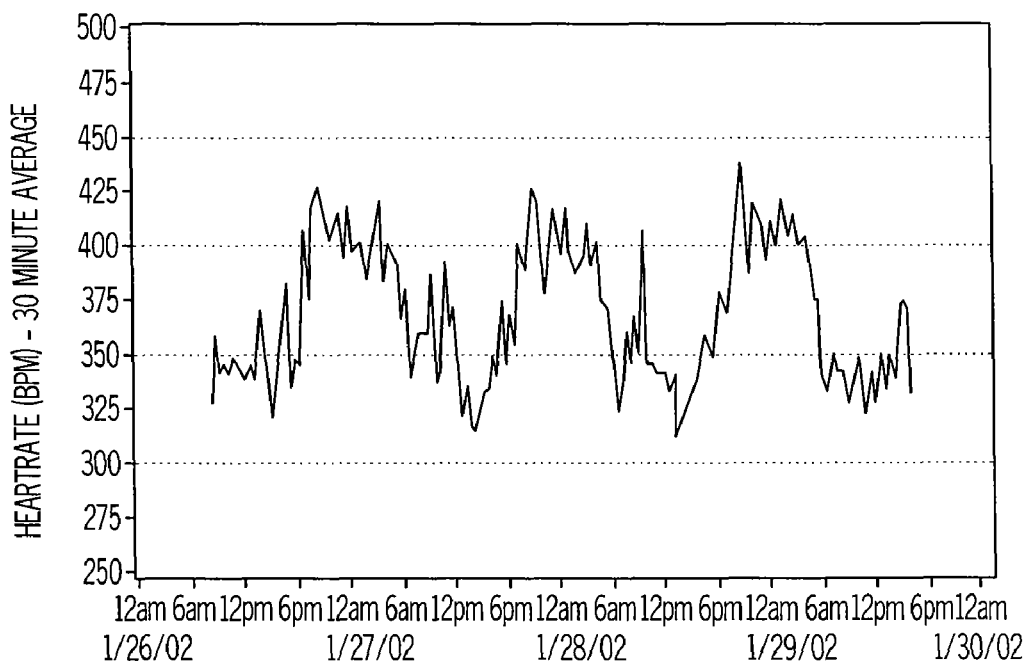
Figure 4E:
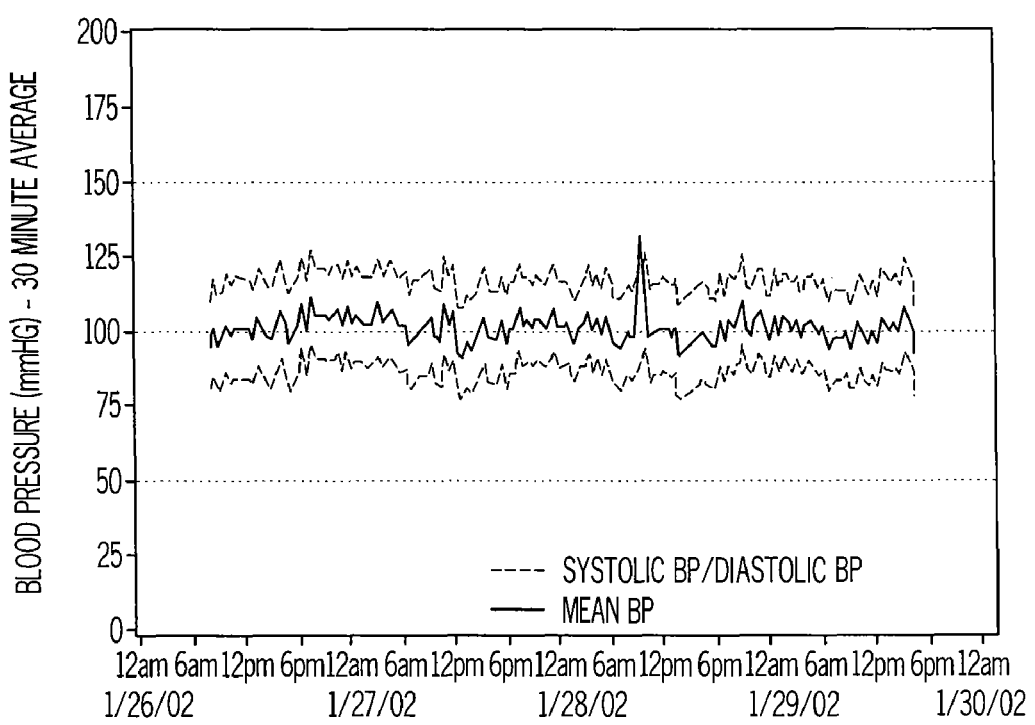

As shown in FIG. 3, in accordance with a second aspect of the present invention, a combination of a dosing device 18 and an automated sample collection machine 20 may be used for both dosing and blood or bodily fluid sample collection. Further, the system 22 may include physiological measurement devices 24, preferably implanted and wireless, which are used to monitor various physiological parameters, also referred to herein as physiological endpoints. Measurement of tidal volume and respiration rate, and the sampling of exhaled breath are also possible in a tidal volume changer 28, as representatively shown in FIG. 1. The combination of dosing, breath, blood or fluid data, and physiological endpoints allow for real-time evaluation of whether a relationship exists and what relationships exist between the dose, kinetics, and/or endpoints in a test animal. FIG. 3 is illustrative of the types of devices that can be used in the system of the present invention with either a retrained or a freely-moving, non-restricted test animal, such as a rodent. Tests on such freely-moving test animals are particularly improved by the fusion of dosing, sampling, and measuring techniques and resulting data analysis and data fusion to control exposure conditions and dosing in accordance with the present invention.

Prior to the advent of automated dosing 18 and automated sample collection machines 20, multiple animals 2 were needed in order to collect blood or bodily fluid samples or the physiological endpoints, but both sampling and measurement of such endpoints was not possible at the same time with the same animal. This was due to the need to sacrifice animals to obtain the requisite samples of blood or bodily fluid. However, by surgically implanting both indwelling catheter(s) 4 and physiological monitoring device(s) 24 in a test animal and exteriorizing the catheter 4 to the automated sample collection machine 24, multiple samples can be collected and electronic signals can be electronically transmitted to a receiver 26 to measure a given physiological endpoint while the animal 2 is freely-moving or restrained. In this way, the kinetics (blood or bodily fluids) and physiological effects of the drug, toxin or other test material can be determined without interference from human contact that can stress the animal, affecting the physiological endpoints.

The automated dosing 18 and automated sample collection machine 20 of FIG. 3 preferably includes the Empis and Culex (available from Bioanalytical Systems, Inc; BASi; W. Lafayette, Ind.) for collection of whole blood samples, or BASi's microdiffusion sampling machine for collection of bodily fluid samples. The automated dosing 18 and sampling collection machines 20 are connected to separate indwelling catheters 4 that are surgically implanted in different blood vessels (Culex) or tissue/organ (microdiffusion) of interest in the animal. The catheters may be specially designed by BASi. As representatively shown in FIG. 3, the Empis dosing machine is connected to the jugular vein 40 of the test animal where intravenous administration of a drug is desired; or alternatively is connected directly to the stomach 44 where oral administration of a drug is desired. Representative sampling, using a Culex machine to sample blood is shown located in the femoral vein 42 of the test animal.

As further shown in FIG. 3, a representative physiological monitoring device 24 is shown, which could be any of various physiological devices 24 with transmitters. The physiological monitoring device is preferably implantable. By way of example and not limitation, the monitoring physiological measurement device 24 could be a sensor for temperature; activity; ocular pressure; EEG readings; EMG; EKG and blood pressure measurements; arterial, venous or left ventricle pressure; pleural pressure; ECG-P, PR, QRS and interval measurements; QT Interval, (GP); or combinations thereof. Signals are picked up by a receiver 26 outside the animal, such as at a cardiotelemetry receiver, as representatively shown in FIG. 3.

The physiological monitoring devices 24, receivers 26, and software for analyzing the output are proprietary products from various companies, by way of example and not limitation, cardiotelemetry devices available from Data Sciences, Inc (DSI). Thus, while the invention of FIG. 3 uses automated dosing and sample collection with a representative cardiotelemetry device, it also may be used with other physiological monitoring devices 24 based on the physiological endpoint of interest and the physiological monitoring device 24 available on the market for use.

Once implanted, these dosing, sampling and measuring devices allow multiple real time, concurrent measurements, rather than periodic measurements via sacrifice, of target analytes, biochemicals, drug levels, biomarkers and other values in the fluids and breath of the same test animal along with concurrent or periodic physiological characteristics. Further, the system of the present invention enables such measurements without stressing animals by handling, eliminating a source of variability in the data.

The present invention thus enables collection of dosing, sampling and physiological monitoring data from which the kinetics and biological and physiological responses of test animals can be measured in real time using the same animal. Moreover, the system may then adjust the exposure of the test animal to achieve or monitor desired biological and physiological parameters in a test animal. The reduced biological variability in the data that results. improves the scientific quality of the data. In addition, this invention reduces the number of animals needed to be tested and sacrificed, since all of the samples and physiological responses can be collected from and generated by the same animal. These advantages also reduce the time and costs associated with the testing, as fewer animals are sacrificed by handling.

Figure 6:
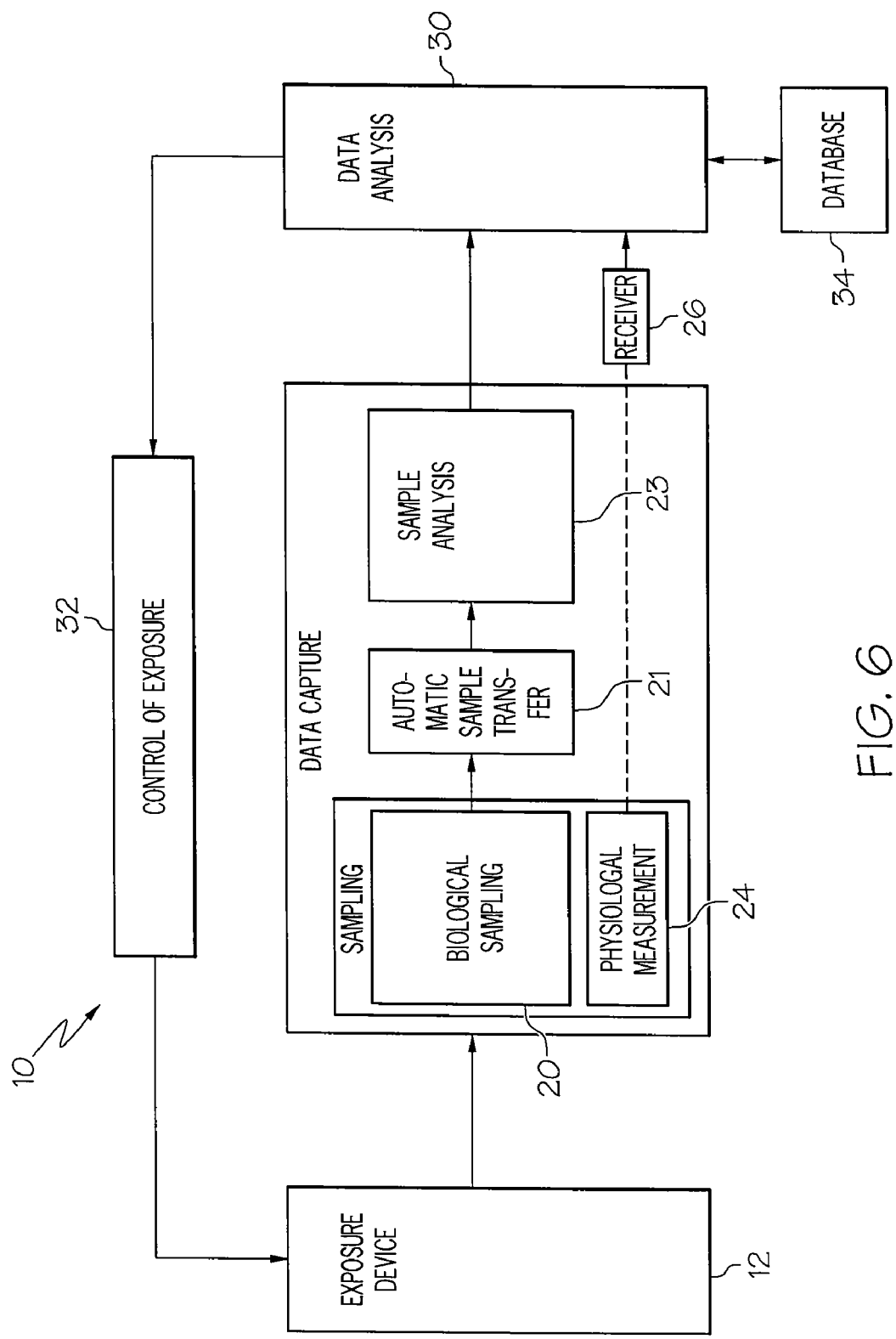
FIG. 6 is a block diagram of the system and method of the present invention.

In a further aspect of the present invention, samples drawn from the test animal are passed either manually or robotically by automatic sample transfer device 21 as indicated in FIG. 6 to an automatic sample analysis device 23 or detection device, including but not limited to technologies such as a mass spectrometer, Raman spectrometer, or other clinical analyzer to measure the target analyte(s) or other biochemical value of interest. Alternatively, in accordance with the present invention, a desired analysis device can be merged with the Culex device or other BASi sampling device to provide immediate analysis without requiring the transfer step.

Figure 2A:
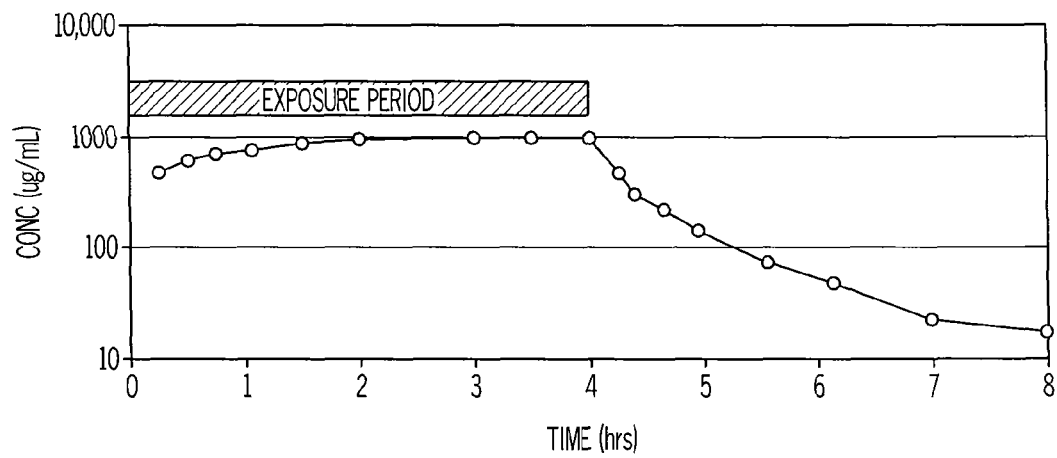
FIGS. 2A-2B show typical output from an automated blood sampling device.
Figure 2B:
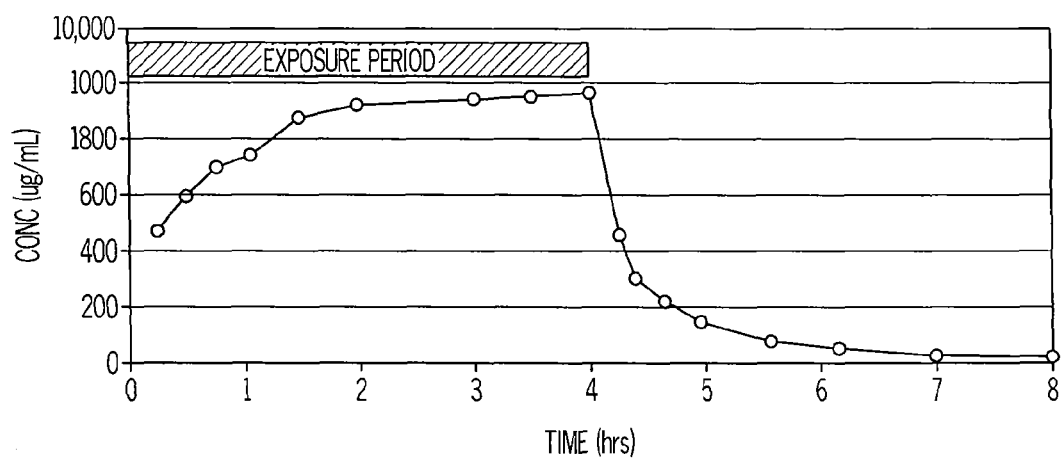

In accordance with the representative system of FIG. 1, the data generated can be used to observe the real effect on the heart of a dose of an injected chemical or drug or other dose of material. Rather than averaging the rates from multiple animals, the real time measurements of dose, blood or other fluid samples, and cardiovascular output, representatively shown in FIG. 2, can be obtained and displayed using commercially available programs. Toxicokinetics can be analyzed using commercially available WinNonLin software, and heart rates displayed through other commercially available software, such as is available from DSI.

This data may be further used to generate toxicodynamic information using commercially available software, such as WinNonLin software available from Pharsight Corporation (Mountain View, Calif.) applied in accordance with the present invention, to generate real time fusion of information.

In a further aspect of the present invention, the output from analysis of the blood or other bodily fluid, from physiological monitoring devices 24, or from values determined by toxicokinetic evaluation, or toxicodynamic analysis can then be used to generate a feedback signal to controller 32 which will then control the dosing of the animal, so that the drug, toxin, or other test material used to dose the test animal is controlled or maintained based on the animal's physiological reaction, biological uptake of a drug, toxin or other test material, time to reach steady state loading of a drug, toxin or other test material after initiation of exposure, the level of a target analyte, or a targeted biomarker, or other values of interest being tested, monitored or maintained. Such other values of a biological parameter may include the presence, level or other value of a blood constituent, which can be determined using capillary tube techniques known in the art; presence, level or other value of a drug, toxin, particulate test materials such as micro and nanoparticles; the presence, level or other measured value of a biochemical, biomarker, protein, cells, cancer cells, macrophage, virus, bacteria, DNA, RNA, mRNA, gene sequences, or other target analytes present in the blood or bodily fluids. As shown in FIG. 6, various sample analysis devices 21 and techniques known in the art may be applied to the samples, including without limitation use of lab-on-a-chip products, HPLC analysis, mass spectrometers, Raman spectroscopy, PCR tests, microarrays, and various assays known in the art for specific chemicals, including without limitation, nicotine, CO, LPS and other chemicals.

The present invention also enables real-time monitoring of test animals and feed-back control of exposure so that the animal can be dosed to reach the threshold of toxicity on a continuing basis.

Where appropriate to the test being performed, the data analysis device, by way of example and not limitation, is a microprocessor, computer or similar analysis device 30. Analysis device 30, may also refer to a database 34 for values which will be accessed to compare to measured values as part of the process of analyzing the biological and physiological parameters measured. The analysis device 30 may then signal a controller to adjust, control or maintain the exposure conditions for the test animal.

The method of the present invention which provides for automatic feedback control of exposure may also be practiced on a plurality of animals to generate a database including real-time data, and thus enhance existing data used to control the system.

Whether the present invention is operated with the feedback control feature or simply to provide the advantage of multiple, serial data collection in real time during and between dosing, the present invention reduces time and costs associated with testing, as well as making possible reduction in biological variability of data in test results by permitting multiple tests of blood, bodily fluids, breath, and physiological endpoints on the same animal, and by eliminating the stressing of test animals. The further benefit of single animal response data permits measurement and analysis of variability between animals of the same group provided for testing, variability between strains of the same specie of test animals, and variability between species; variability otherwise missed in the prior practice of averaging data obtained by conventional methods over test animal groups.

Figure 5A:
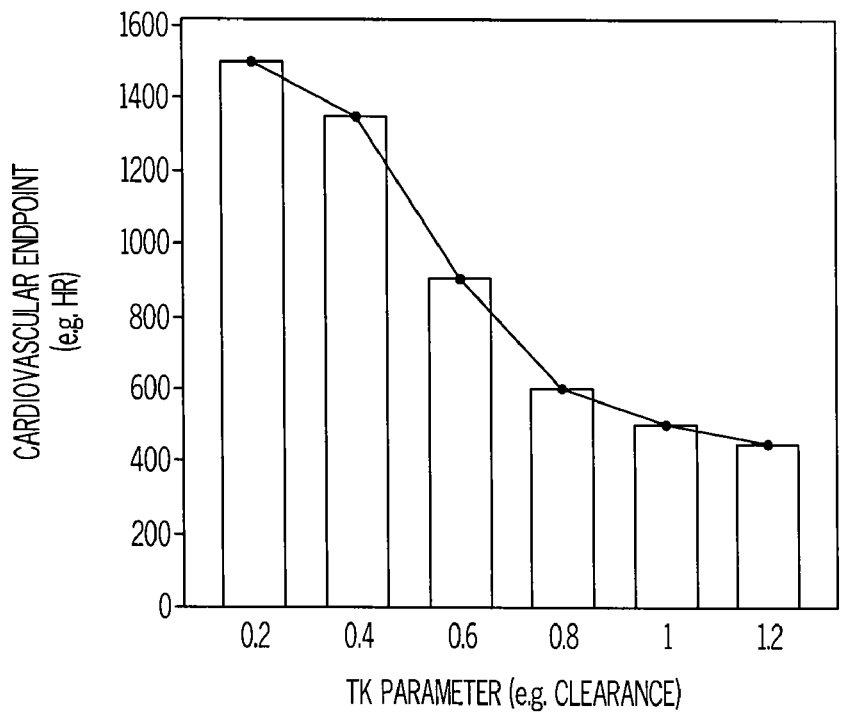
FIG. 5 shows a typical representative result of analysis of multiple data inputs from a single test animal.
Figure 5B:
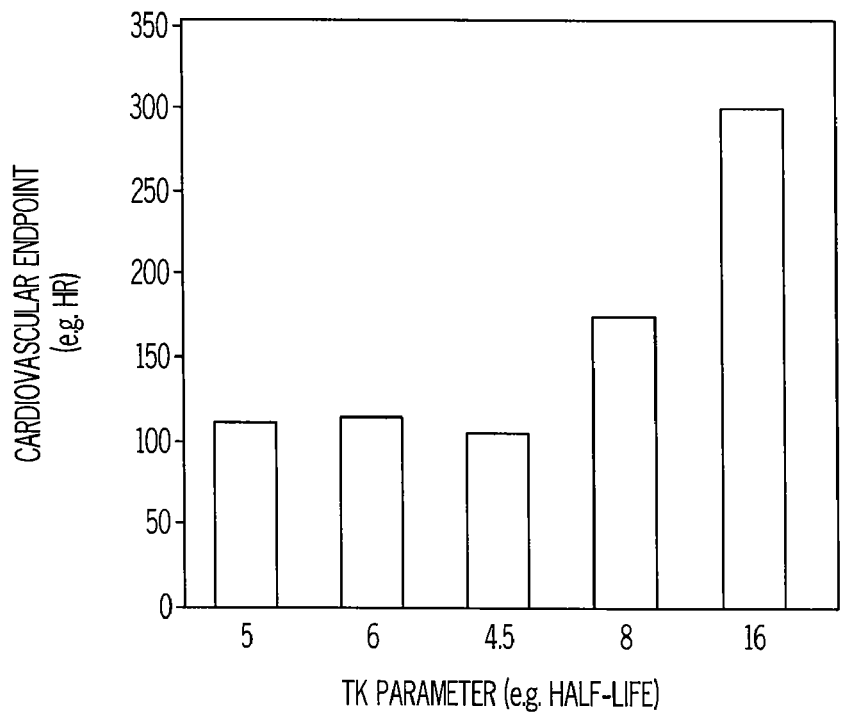

Utilization of the inventions and procedures described above could be used to conduct pharmacokinetic (PK)/toxicokinetic (TK) and ADME (absorption, distribution, metabolism, and elimination) studies, as shown in FIGS. 5A and 5B, thereby allowing the quality of these types of studies to benefit.

Further, the present invention and its procedures described above could also be used to manage cross-over study design more effectively. In cross-over studies where each of the test animals s on the study receives all of the different treatments being studied. This is achieved by first distributing the animals across all treatment groups and initiating the treatment. Upon completion of the treatment and after a wash-out period that assures complete recovery from the treatment, the animals are redistributed across all treatment groups in a manner that allows each animal to receive a different treatment. This process is repeated until all animals have been given all treatments. The conduct of each treatment, and monitoring of the wash-out period and recovery can be more precise in accordance with the present invention to assure that test design conditions have been met, and subsequently complete recovery of a test animal has been achieved.

Thus in sum, the method of the present invention comprises exposing one or more test animals 2 to a drug, toxin or other test material in accordance with a test protocol, and capturing real-time data related to the status of a test animal under test. The real-time data preferably includes one or more of data from a blood or fluid sample withdrawn via a catheter and analyzed to determine a biological parameter. In addition, breath samples may be taken and analyzed. The real-time data also preferably includes one or more measurements of a physiological parameter taken without manually handling the test animal. The combinations of such real-time data are then used in accordance with the present invention to control the exposure conditions in real-time, without the delay and variability of result found in the prior art due to the need to sacrifice test animals to obtain biological samples.

By repeating the steps of exposing, capturing, comparing, and automatically controlling the system, we can maximize the value of animal research.

The method of the present invention may be further practiced to develop animal models by determining their sensitivities to various drugs, toxins or other test materials with greater real time precision. Decision making regarding the selecting or excluding of individual animals for breeding in accordance with the presence, level or other value of one or more of a biological parameter, physiological parameter or combinations thereof can be done with greater certainty, and reduce the time to develop meaningful animal models. Further, the present invention makes possible the analysis of biological parameters and physiological parameters during transition periods as well as during steady state dosing, which can reveal characteristic sensitivities and responses not previously available with convention techniques.

Animal model development can become even more targeted through selective breeding for desired traits, such as sensitivity or insensitivity to the wide variety substances with which the animal are dosed. Such substances, include but are not limited to drugs, chemicals, particulates and biological agents in various forms including but not limited to as aerosols, fluids, fibers, particles, tablets, food, genes, cells, viruses, by various routes of administration discussed above.

As well, the present invention will enable more rapid identification of preferred species of animals for use in animal testing models, based on real-time observations biological and physiological parameters that demonstrate their relative sensitivities to drugs, toxins and other test materials.

The principle and mode of operation of this invention have been described in its preferred embodiments. However, it should be noted that this invention may be practiced otherwise than as specifically illustrated and described without departing from its scope.

What is claimed is:

1. A method for automatic exposure control of a single test animal based on real-time data collected from the single test animal, comprising the steps of:
   a) providing a single test animal having at least one implanted catheter, and optionally, at least one implanted monitoring device;
   b) simultaneously:
      i) exposing the single test animal of step a) to at least one test condition, and
      ii) capturing multiple measurements of samples, over a period of time, from the same single test animal to provide real-time data related to the status of the same single test animal under test with no human-animal contact during testing, wherein the real-time data comprises same single test animal generated responses, over time, to the test condition, and wherein the test condition comprises one or more of a biological parameter, physiological parameter, or combinations thereof;
   c) comparing the real-time data of step b) from the same single test animal to a database of prior generated data from the same single test animal; and
   d) automatically controlling the conditions of the test to which the same single test animal is exposed to produce further real-time data by automatically adjusting the test conditions in response to the same single test animal's response to the test and to the real-time data being captured from the same single test animal.

2. The method of claim 1 wherein the step of capturing the real-time data comprises
   automatically drawing multiple samples of blood or other fluid via the catheter from the same single test animal, absent human-animal contact during testing; and
   analyzing the samples to determine the biological parameter of the same single test animal.

3. The method of claim 2 wherein the step of analyzing the biological parameter comprises determining the presence, level, change in level and/or other value of a blood constituent, drug, toxin, other test material, biochemical, biomarker, protein, cell, macrophage, virus, bacteria, DNA, RNA, mRNA, gene sequence, or other target analyte.

4. The method of claim 2 wherein
   the step of capturing real-time data from the same single test animal further comprises automatically transferring the multiple samples to a sample analysis device, absent human-animal contact during testing; and
   the step of analyzing further comprises preparing the multiple samples for analysis, absent human-animal contact during testing.

5. The method of claim 2 wherein the step exposing the same single test animal to the test condition, and the step of capturing multiple measurements of samples, are performed using the separate catheters.

6. The method of claim 1 wherein the step of comparing comprises: determining the biological uptake; evaluating toxicokinetic effect; assessing toxicodynamics of a drug, toxin or other test material; or combinations thereof.

7. The method of claim 1 wherein the same single test animal also has an a monitoring device implanted therein, wherein the step of capturing multiple measurements of samples, over a period of time, from the same single test animal to provide real-time data of the physiological parameter comprises measuring, using the implanted monitoring device, one or more of: motion, temperature, ocular pressure, interperitoneal pressure, EEG readings, EMG, EKG, blood pressure, venous pressure, left ventricle pressure; pleural pressure, ECG-P, PR, QRS and interval measurements, QT interval, GP, or combinations thereof.

8. The method of claim 1 wherein the step of automatically controlling comprises automatically adjusting conditions of the test, and responsively producing multiple measurements of real-time data from the same single test animal at a value relative to one or more reference values, absent human-animal contact during testing.

9. The method of claim 8 where the step of responsively producing multiple measurements of real-time data comprises maintaining the value of the biological parameter at a desired level over a period of time.

10. The method of claim 9, wherein the biological parameter is the level or change in level of a drug, toxin or test material in a test animal.

11. The method of claim 1 wherein the step of exposing the same single test animal to the test condition comprises at least one of delivering at least one drug, toxin or other test material to the same single test animal by inhalation, intravenous administration, injection, whole body exposure, ingestion, installation, implantation, stomach tube, administration through a bodily orifice, or combinations thereof.

12. The method of claim 1 wherein the method further comprises repeating the steps of exposing, capturing, comparing and controlling using the same single test animal.

13. The method of claim 12 further comprising the step of selecting or excluding the same single test animal for breeding in accordance with the presence, level or other value of one or more of the biological parameter, physiological parameter or combinations thereof.

14. The method of claim 12 wherein the method further comprises the step of providing automatic feedback of the real-time data to the data base for generating a database including the real-time data.

15. The method of claim 12 wherein after the step of repeating exposing, capturing, comparing and automatically controlling is performed in accordance with a test protocol, the method further comprises:
   repeating the steps of capturing and comparing; and
   monitoring the health status of the same single test animal.

16. The method of claim 1 wherein the physiological monitoring device comprises an implanted monitoring device having a wireless transmitter.

17. The method of claim 1 further including generating a feedback signal to control one or more of: the step of exposing the same single test animal to the test condition, and the step of capturing multiple measurements of samples from the same single test animal.

18. The method of claim 17, wherein the same single test animal is exposed to the test condition at a threshold of toxicity on a continuing basis.

* * * * *